United States Patent [19]

Beckham

[11] 4,340,148
[45] Jul. 20, 1982

[54] LUER CAP

[75] Inventor: David S. Beckham, Fox Lake, Ill.

[73] Assignee: Baxter Travenol Laboratories, Inc., Deerfield, Ill.

[21] Appl. No.: 196,988

[22] Filed: Oct. 14, 1980

[51] Int. Cl.³ .................. B65D 41/04; B65D 41/34
[52] U.S. Cl. ............................ 215/329; 215/320;
215/247; 128/214 R; 128/272
[58] Field of Search .............. 215/329, 320, 247;
128/214 R, 272

[56] References Cited

U.S. PATENT DOCUMENTS 3,815,769  6/1974  Rapoza et al. ................. 215/329
4,133,312  10/1976  Burd ........................... 128/214 R Primary Examiner—George T. Hall
Attorney, Agent, or Firm—Paul C. Flattery; Thomas R. Schuman; John A. Caruso

[57] ABSTRACT

A luer cap for use on ports of medical devices such as cardiotomy reservoirs and blood sets. The cap comprises an outer wall (10) having a generally circular cross-sectional shape. An inner wall (12) and end wall (20) define an internal port receiving cavity (13). The inner wall (12) is threaded to mate with threads or a flange on a female luer port. The mating surfaces of the luer cap and the luer port can be sterilized through a hollow tubular portion (18), end wall (20), and outer wall (10) of the luer cap.

13 Claims, 5 Drawing Figures

LUER CAP

BACKGROUND OF THE INVENTION

This invention relates to an improved luer cap for medical devices, principally for use on medication ports, connecting ports, and injection ports of medical devices.

Many medical devices such as cardiotomy reservoirs, blood sets, and oxygenators have ports for access to the devices. Since many of the devices process a patient's blood for a variety of medical treatments, e.g., oxygenation of blood during a heart-lung bypass operation, it is frequently necessary that a physician, nurse, or medical technician have access to the device to add medication to the patient's blood or to take a blood sample. Because of this need, many medical devices have ports which are covered by a protective cap. When access is necessary, the caps are removed to uncover the port.

The major problem with prior art port caps is the inability to sterilize through the cap once it is placed on a port in the manufacturing process. An additional problem is that, prior to this invention, no luer cap was available through which sterilization could occur and which would not leak air or liquid when subjected to a positive or negative pressure during operation of the device.

The term "luer" is derived from the name of a German instrument maker who developed a medical syringe in the Nineteenth Century. The term "luer-lok" is defined in Dorland's Illustrated Medical Dictionary, 25th Edition, as "a glass syringe for intravenous and hypodermic use, with a metallic tip and locking device to hold the needle firmly in place."

FIGS. 3 and 4 of U.S.A. Standard Z70.1-1955, "Dimensions of Glass and Metal Luer Tapers for Medical Applications," show respectively female luer lock and male luer lock connectors. Burd U.S. Pat. No. 4,133,312 shows a luer lock connection used with a blood tubing set.

The structure of U.S.A. Standard Z70.1-1955, "Dimensions of Glass & Metal Luer Tapers for Medical Applications", (FIG. 4 of the Standard), and the structure of the blood tubing set connector of Burd U.S. Pat. No. 4,133,312 cannot perform the sterilizing function of the present invention since their tubular portions are open. Additionally, the U.S.A. Standard and Burd U.S. Pat. No. 4,133,312 are connectors for fluid flow and cannot perform a capping function like the present invention.

Before this invention, a practice was to supply medical devices with sterile ports covered by protective tabs. Caps for these ports were supplied separately. Before the medical device was placed into operation, the tabs on the ports were removed and the caps put in place. There was concern on the part of medical personnel for maintenance of sterility of the system when the caps were put in place. A reason that medical devices, prior to this invention, were not supplied with the port caps in place was that the gas used to sterilize the medical device could not pass through the cap and reach, and therefore sterilize, the portion of the device (port area) covered by the cap.

Thus, there is a need to provide a luer cap for ports of medical devices through which sterilization can occur and which will not leak air or liquid when subjected to a positive or negative pressure during operation of the device. The ability of the luer cap to not leak air or liquid during positive or negative pressurization of the medical device is significant since many medical devices operate above (positive) or below (negative) atmospheric pressure. If the device is subjected to a negative pressure, and the luer cap leaks, the potential for airborne contamination entering the device is high. If the device is subjected to a positive pressure, and the luer cap leaks, blood or other body fluid could escape from the device to the potential severe detriment of the patient.

A cap which is simple in design is also desirable for ease of molding and manufacture.

It is, therefore, an object of this invention to provide an improved luer cap for medical devices which is of simple design, and when placed on a port of a medical device, the port can be sterilized through the luer cap. It is a further object of this invention to provide an improved luer cap which will not leak air or liquid when subjected to a positive or negative pressure during use of the device.

These objects are satisfied by the present invention which incorporates a luer cap design which is permeable to ethylene oxide gas (ETO) and can be placed on a device prior to ETO sterilization. The design is also capable of withstanding the positive or negative pressures that the medical device may be subjected to during use.

SUMMARY OF THE INVENTION

The luer cap of the present invention is a male luer cap capable of providing an engagement with an external wall of a female luer port; the female luer port can be either externally threaded or have a single projection or flange at its distal end. After the male luer cap is engaged with the female luer port, all mated surfaces are capable of being sterilized by ethylene oxide gas sterilization through the male luer cap. The luer cap has a wall thickness and is made of a plastic material such that efficient ETO sterilization occurs. The connection between the male luer cap and the female luer port is sufficiently secure to enable pressurization of the connection during use of a medical device which uses the luer cap of this invention.

The present invention male luer cap comprises a generally circular cross-sectional outer wall. There is an inner wall which is internally threaded and an end wall which define an internal port receiving cavity. The end wall extends into the cavity and defines a hollow tubular portion which has an open end and a closed end. Sterilizing gas passes through the outer wall, the hollow tubular portion, and the end wall to sterilize all interior surfaces of the male luer cap and female luer port. The cap is fabricated of a plastic which is permeable to ethylene oxide gas and which enables ethylene oxide gas to pass through the cap and effect sterilization. The preferred plastic is manufactured and supplied by Celanese Corporation under the trade name CELCON, and is generically an acetal copolymer. The preferred thickness of the hollow tubular portion and the preferred thickness of the end wall is in the range 0.018 to 0.022 inches.

BRIEF DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE PREFERRED EMBODIMENT

The preferred embodiment of the luer cap of this invention is illustrated in FIGS. 1-4.

Figure 1:
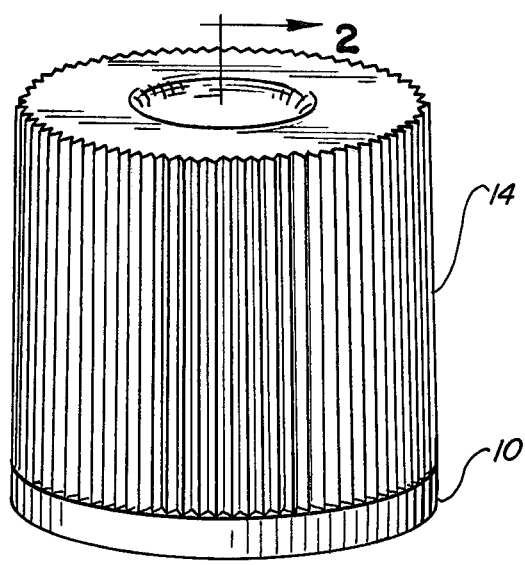
FIG. 1 is a greatly enlarged perspective view of the luer cap of the present invention.

Referring to FIG. 1, the inventive luer cap is shown in perspective view with an outer wall 10 of generally circular cross-sectional configuration. There is a knurled portion 14 on the outer wall 10 to aid in manually grasping the luer cap and also to aid in removing the luer cap from the mold during fabrication of the luer cap.

Figure 2:
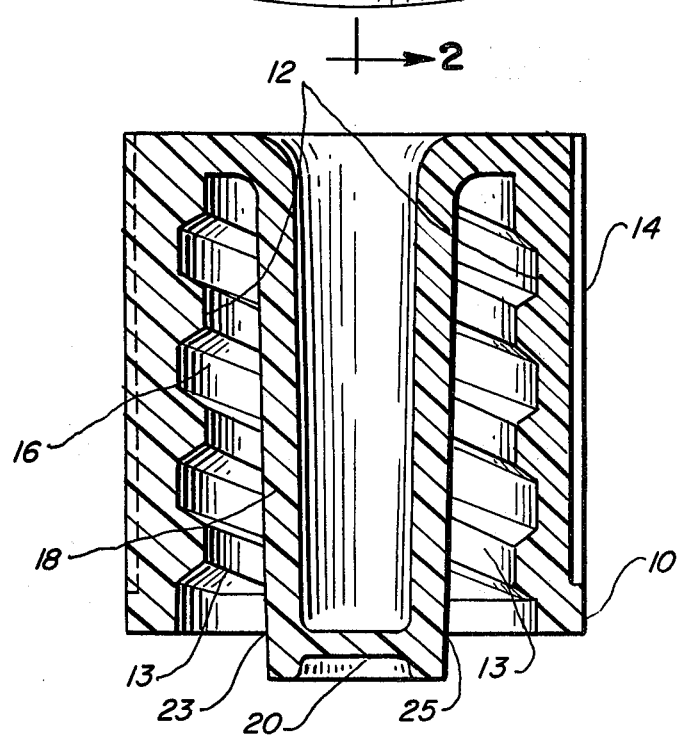
FIG. 2 is a longitudinal sectional view of the preferred embodiment of the luer cap of this invention, taken along line 2—2 of FIG. 1.
Figure 3:
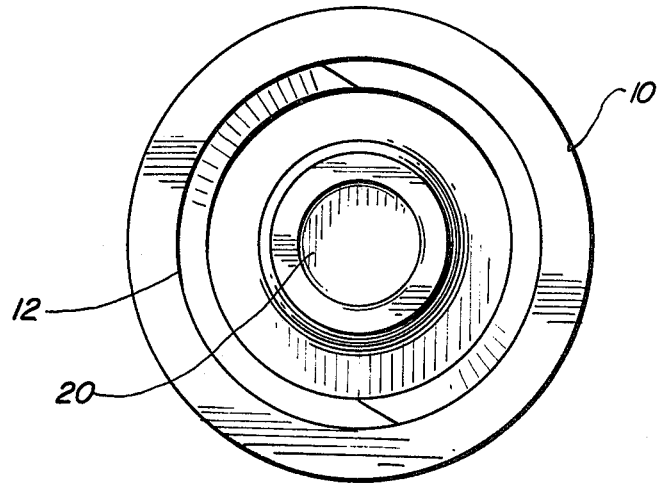
FIG. 3 is a bottom view of the luer cap.

Referring to FIG. 2, the luer cap of FIG. 1 is shown in longitudinal section taken along line 2—2 of FIG. 1. An internal port receiving cavity 13 is defined by an inner wall 12 and an end wall 20. The inner wall 12 has threads 16 exterior to and surrounding a hollow tubular portion 18.

The hollow tubular portion 18 of the luer cap is closed by end wall 20 at one end and is open to the atmosphere at the end of the hollow tubular portion 18 which is opposite end wall 20.

In the preferred embodiment which is shown in FIG. 2, the end wall 20 is shown at the distal end of hollow tubular portion 18, but the end wall 20 can be at any vertical location along hollow tubular portion 18.

During ethylene oxide gas sterilization of a medical device having a female luer port with a luer cap of this invention attached to it, ethylene oxide gas passes inside and down hollow tubular portion 18 and passes through hollow tubular portion 18 to sterilize the mated surface of the female luer port. The sterilizing gas also passes through end wall 20 to aid sterilization at mating points 23 and 25.

The exterior surface of the female port and the threads 16 of the male luer cap are sterilized by ethylene oxide gas permeating through wall 10. Wall 10 is of such a material and thickness so that the sterilizing gas can permeate through wall 10, yet wall 10 is structurally strong.

The preferred plastic from which the luer cap of this invention is fabricated is CELCON, a trade name of a generic acetal copolymer manufactured and supplied by Celanese Corporation. CELCON has an inherent lubricity which prevents it from binding with rigid plastics such as polycarbonates and plexiglass which are used in many medical devices. The preferred wall thickness of hollow tubular portion 18, end wall 20, and outer wall 10 is 0.020 inch, and the preferred range is 0.018 to 0.022 inches. It has been found that these wall thicknesses result in the luer cap being sufficiently permeable so that enough ETO can pass through the cap to effect sterilization. 100% ETO gas is required for sterilization, not a mixture of ETO gas and freon as is sometimes used in the sterilization art.

Figure 4:
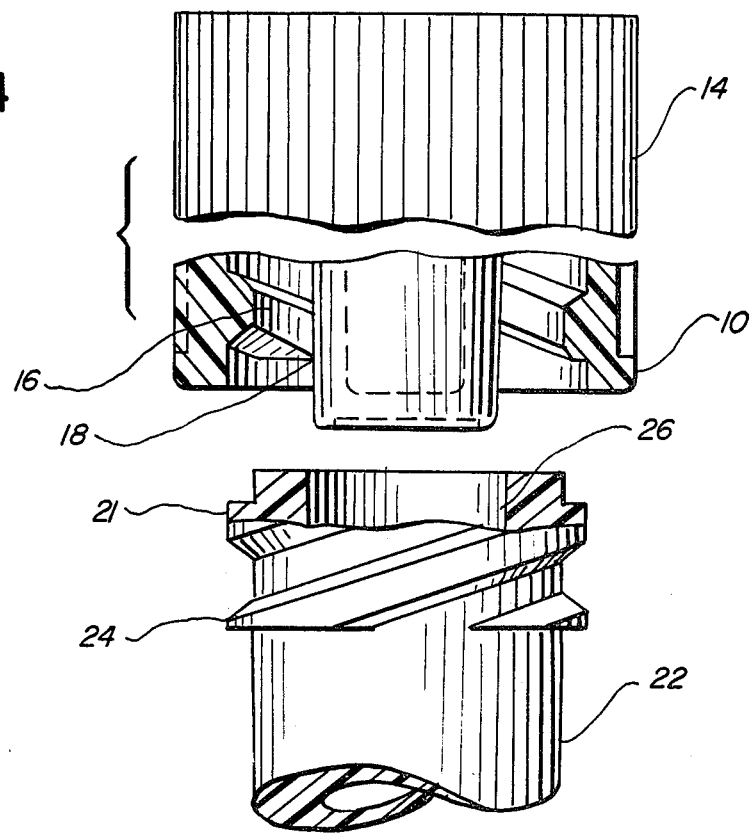
FIG. 4 is a perspective view, with portions shown in longitudinal sectional view, of the luer cap of this invention shown about to be mated with a female luer port.

Referring to FIG. 4, the male luer cap of the present invention with outer wall 10 is shown in perspective view with portions broken away as it prepares to engage with outer wall 21 of female luer port 22. When the male luer cap of the present invention is engaged with the female luer port 22, internal threads 16 of the male luer cap mate with the external threads 24 of outer wall 21 of female luer port 22, and hollow tubular portion 18 of the male luer cap mates with axial bore 26 of the female luer port. Alternatively, internal threads 16 of the male luer cap can mate with a female luer port which has a single flange circumferentially formed around the distal end of female luer port 22.

Because the design of the present invention includes hollow tubular portion 18 with end wall 20, and because of the nature and thickness of the material used in its fabrication (CELCON having a thickness in the range of 0.018 to 0.022 inches), during ETO sterilization, ethylene oxide gas migrates inside and down and through hollow tubular portion 18 and through end wall 20 to sterilize axial bore 25 of female luer port 22. Thus, the mated surfaces of the male luer cap and the female luer port are sterilized prior to shipment with the male luer cap shipped in place.

Figure 5:
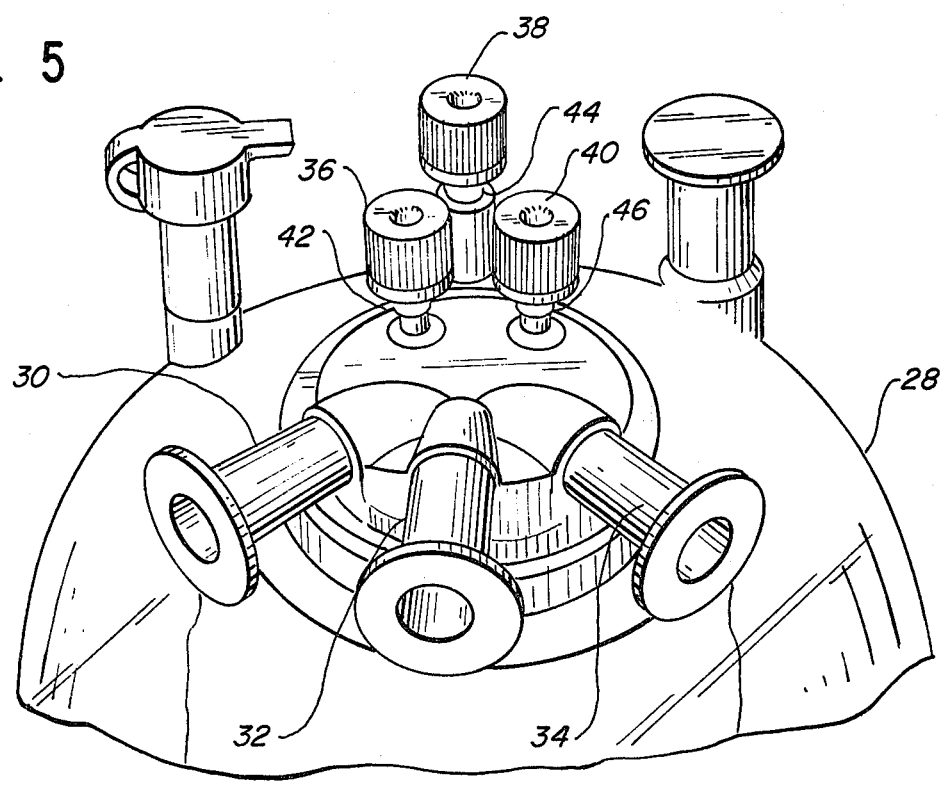
FIG. 5 is a partial perspective view of the top portion of a cardiotomy reservoir using the luer cap of this invention.

Referring to FIG. 5, a commercial cardiotomy reservoir with overhead inlets is shown in partial cutaway perspective view. The device is manufactured and sold by the Artificial Organs Division of Travenol Laboratories, Inc., Deerfield, Ill. as a Model 1470 Cardiotomy Reservoir. It is used in conjunction with a heartlung machine to store and filter blood returned from the surgical field.

The cardiotomy reservoir of FIG. 5 consists of an outer plastic housing 28 with three overhead noncommunicating suction inlets 30, 32, and 34. These suction inlets are connected to blood suction lines that remove blood from the surgical field during open heart surgery.

Luer caps of the present invention are shown at 36, 38, and 40 covering female luer ports 42, 44, and 46 which are used for the administration of blood, fluids, and medication; the ports are also used to monitor pressure within the device. Prior to the male luer cap of this invention, the caps 36, 38, and 40 had to be shipped separated from the luer ports 42, 44, and 46 of the cardiotomy reservoir, and the luer caps were placed on the reservoir in the operating room. This is less desirable than having the caps in place and sterilized when the reservoir is unpackaged and ready to use.

The present invention satisfies a long felt need for a luer cap through which sterilization can occur enabling shipment of medical devices with luer caps in place. It also satisfies the need for a cap which will hold pressure under operating conditions of the various medical devices with which the present invention can be used. The design is simple and easy to mold and manufacture.

While the present invention has been disclosed in connection with the preferred embodiment thereof, it should be understood that there may be other embodiments, which fall within the scope of the invention as defined by the following claims.

What is claimed is:

1. In a medical device having a port comprising an annular wall, an axial bore defined within said annular wall, and thread engaging means carried by said annular wall, the improvement comprising, in combination: a cap mounted on said port, said cap comprising a circular sidewall having an inside wall surface;

a hollow tubular portion disposed interior of said sidewall and defining an internal port-receiving cavity between and defining an internal port-receiving cavity between said tubular portion and the inside surface of said sidewall for receiving said annular wall of said port, said hollow tubular portion of said cap being disposed within the bore of said port when said annular wall of said port is received within said port-receiving cavity;

said hollow tubular portion being closed at one end by an end wall and open to the atmosphere at the opposite end; and the inside surface of said cap sidewall carrying threads for engagement with the thread engaging means of said annular wall of said port.

2. A medical device in accordance with claim 1 wherein said cap is made of acetal copolymer plastic material and said tubular portion and said end wall are of selected thickness for permeability of sterilizing gas to effect sterilization of said port.

3. A medical device in accordance with claim 2 wherein said cap is made of CELCON plastic.

4. A medical device in accordance with claim 3 wherein said selected thickness is in the range of 0.018 to 0.022 inches.

5. A medical device in accordance with claim 2 wherein said selected thickness is in the range of 0.018 to 0.022 inches.

6. A medical device in accordance with claim 4 wherein said selected thickness is about 0.020 inches.

7. A medical device in accordance with claim 5 wherein said selected thickness is about 0.020 inches.

8. A circular cap for a female Luer connector port comprising:

an annular sidewall;

a wall defining a hollow tubular portion interior of said sidewall and defining an internal port-receiving cavity between said tubular portion and the inside surface of said annular sidewall;

said tubular portion being closed at one end by an end wall and open to the atmosphere at the opposite end, and defining a substantially continuous Luer taper in the direction of said closed end for close-fitting engagement with the interior surface of a female Luer connector;

said cap being made of acetal copolymer, and said end wall and said wall defining said hollow tubular portion being of selected thickness for gas permeability to effect sterilization of said female Luer connector.

9. A cap in accordance with claim 8 wherein said cap is made of CELCON plastic material.

10. A cap in accordance with claim 8 wherein said selected thickness is in the range of 0.018 to 0.022

11. A cap in accordance with claim 9 wherein said selected thickness is in the range of 0.018 to 0.022 inches.

12. A cap in accordance with claim 10 wherein said selected thickness is about 0.020 inches.

13. A cap in accordance with claim 11 wherein said selected thickness is about 0.020 inches.

* * * * *